US009721176B2

(12) United States Patent
Prager

(10) Patent No.: US 9,721,176 B2
(45) Date of Patent: Aug. 1, 2017

(54) SUPPLEMENTAL DEVICE FOR GATHERING INFORMATION CONCERNING THE USE OF AN INJECTION DEVICE

(71) Applicant: SANOFI-AVENTIS DEUTSCHLAND GMBH, Frankfurt am Main (DE)

(72) Inventor: Roman Prager, Ganserndorf (AT)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 110 days.

(21) Appl. No.: 14/783,169

(22) PCT Filed: Apr. 16, 2014

(86) PCT No.: PCT/EP2014/057777
§ 371 (c)(1),
(2) Date: Oct. 8, 2015

(87) PCT Pub. No.: WO2014/173768
PCT Pub. Date: Oct. 30, 2014

(65) Prior Publication Data
US 2016/0045278 A1 Feb. 18, 2016

(30) Foreign Application Priority Data

Apr. 22, 2013 (EP) ..................................... 13164748

(51) Int. Cl.
G06K 9/20 (2006.01)
A61B 19/00 (2006.01)
(Continued)

(52) U.S. Cl.
CPC ........ G06K 9/2063 (2013.01); A61B 19/5212 (2013.01); A61M 5/24 (2013.01);
(Continued)

(58) Field of Classification Search
None
See application file for complete search history.

(56) References Cited

U.S. PATENT DOCUMENTS

2006/0224123 A1* 10/2006 Friedli ............. A61M 5/31525
604/207
2012/0022458 A1* 1/2012 Oh .................... A61M 5/31551
604/189
(Continued)

FOREIGN PATENT DOCUMENTS

WO 2006/120182 11/2006
WO 2011/117212 9/2011
(Continued)

OTHER PUBLICATIONS

European Search Report for EP Application No. 13164748, completed Oct. 15, 2013.
(Continued)

Primary Examiner — Matthew Bella
Assistant Examiner — Soo Shin
(74) Attorney, Agent, or Firm — McDonnell Boehnen Hulbert & Berghoff LLP

(57) ABSTRACT

A supplemental device for gathering information concerning the use of an injection device, the supplemental device having a first camera sensor portion for generating a first camera output indicative of a scene in the field of view of the first camera sensor portion, a second camera sensor portion for generating a second camera output indicative of a scene in the field of view of the second camera sensor portion, and at least one processor. The processor configured to use the first camera output to determine whether a rotational speed of an object in the field of view exceeds a threshold speed, if it is determined the rotational speed of the object does not exceed the threshold speed, to process the second camera output to identify a feature provided on the or another object, (Continued)

and if it is determined the rotational speed of the object does exceed the threshold speed, to refrain from attempting to identify the feature.

16 Claims, 5 Drawing Sheets

(51) Int. Cl.
*A61M 5/315* (2006.01)
*A61M 5/24* (2006.01)
*H04N 7/18* (2006.01)
*H04N 5/247* (2006.01)
*H04N 5/225* (2006.01)
*A61M 5/31* (2006.01)

(52) U.S. Cl.
CPC ...... *A61M 5/31525* (2013.01); *H04N 5/2253* (2013.01); *H04N 5/247* (2013.01); *H04N 7/181* (2013.01); *A61M 2005/3126* (2013.01); *A61M 2205/3306* (2013.01); *A61M 2205/50* (2013.01); *A61M 2205/52* (2013.01); *A61M 2205/6063* (2013.01)

(56) References Cited

U.S. PATENT DOCUMENTS

| | | | |
|---|---|---|---|
| 2012/0215162 A1* | 8/2012 | Nielsen | A61M 5/3155 604/65 |
| 2013/0197445 A1* | 8/2013 | Schabbach | A61B 5/14532 604/189 |
| 2014/0194825 A1* | 7/2014 | Nielsen | A61M 5/24 604/189 |
| 2014/0194826 A1* | 7/2014 | Nielsen | A61M 5/24 604/189 |

FOREIGN PATENT DOCUMENTS

| | | |
|---|---|---|
| WO | 2013/004843 | 1/2013 |
| WO | 2013/004844 | 1/2013 |

OTHER PUBLICATIONS

International Search Report and Written Opinion for Int. App. No. PCT/EP2014/057777, mailed Jun. 4, 2014.

* cited by examiner

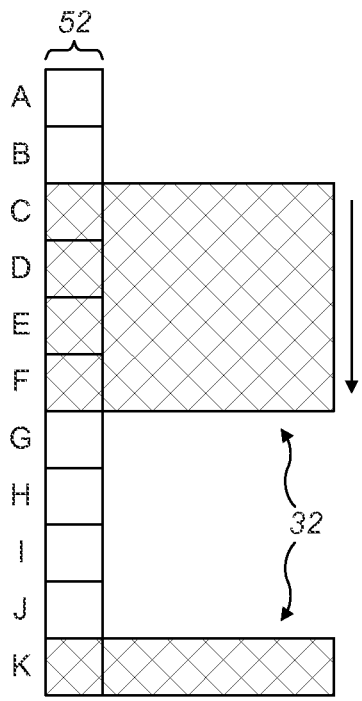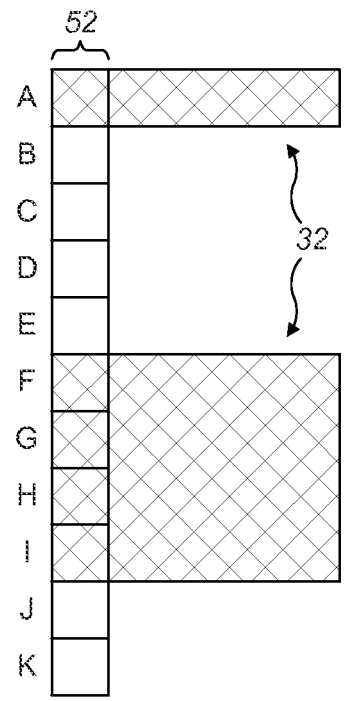
FIG. 6     FIG. 7
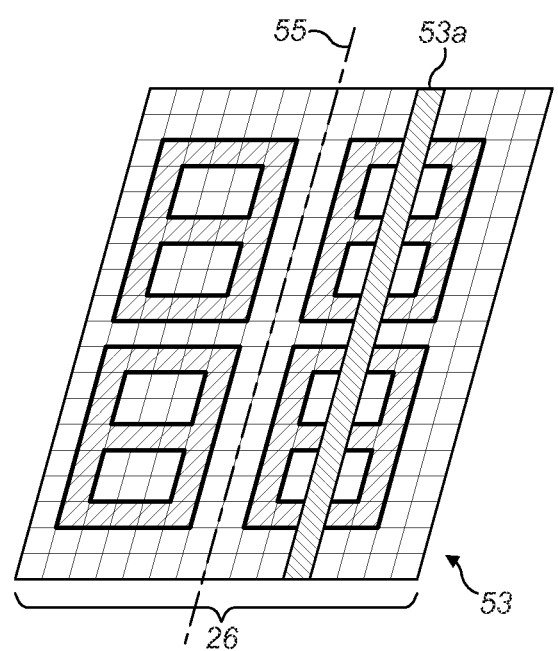
FIG. 8

SUPPLEMENTAL DEVICE FOR GATHERING INFORMATION CONCERNING THE USE OF AN INJECTION DEVICE

CROSS REFERENCE TO RELATED APPLICATIONS

The present application is a U.S. National Phase Application pursuant to 35 U.S.C. §371 of International Application No. PCT/EP2014/057777 filed Apr. 16, 2014, which claims priority to European Patent Application No. 13164748.9 filed Apr. 22, 2013. The entire disclosure contents of these applications are herewith incorporated by reference into the present application.

FIELD OF THE INVENTION

The present invention relates to a device for gathering information concerning the use of an injection device and relates particularly, but not exclusively, to a supplemental device for gathering information concerning the use of an injection device which is used to inject medicament such as insulin.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses that are administered. Supplemental devices may be used to record information about the various times at which insulin doses are administered and the quantity of insulin administered during each such dose.

One previously proposed insulin injection device, specifically the Solostar™ injection pen sold by Sanofi, is provided with a window in its outer surface. A sleeve inside the Solostar™ injection pen (known as the number sleeve) is caused to rotate when an amount of insulin is dialled or dispensed. Numbers on the number sleeve successively align with the window as the sleeve rotates. When an amount of insulin has been dialled, the number corresponding to the dialled amount of insulin (in International Units) is displayed in the window. When insulin is dispensed, rotation of the number sleeve causes the number displayed in the window to be that associated with the dialled amount of insulin remaining in the pen yet to be dispensed.

It has been proposed for a supplemental device to gather information on how much insulin is delivered from a Solostar™ injection pen by analysing information displayed in the above mentioned window. In particular WO2011/117212 describes a supplemental device provided with optical character recognition (OCR) functionality for reading numbers aligned with the window of an injection device to determine quantities of insulin dialled or delivered.

Problems arise however when the number sleeve is caused to rotate above a certain speed. When this occurs numbers displayed in the window appear blurry to the supplemental device, thereby hindering the supplemental device from gathering information concerning the quantity of insulin dialled or dispensed.

SUMMARY

According to an aspect of the present invention there is provided a supplemental device for gathering information concerning the use of an injection device, the supplemental device comprising:
a first camera sensor portion for generating a first camera output indicative of a scene in the field of view of the first camera sensor portion;
a second camera sensor portion for generating a second camera output indicative of a scene in the field of view of the second camera sensor portion; and
at least one processor configured:
to use the first camera output to determine whether a rotational speed of an object, e.g. a sleeve of an injection device, in the field of view exceeds a threshold speed;
if it is determined the rotational speed of the object, e.g. sleeve, does not exceed the threshold speed, to process the second camera output to identify a feature provided on the or another sleeve; and
if it is determined the rotational speed of the object, e.g. sleeve, does exceed the threshold speed, to refrain from attempting to determine the feature.

The processor thus refrains from attempting to determine a feature when the threshold speed is exceeded. Advantageously, this reduces the overall power consumption of the supplementary device.

The supplemental device may be configured for attachment, e.g. releasably attachment, to an injection device.

The first camera sensor portion may generate first camera output at a first rate and the second camera sensor portion may generate second camera output at a second, slower, rate.

Advantageously, this provides that the first camera output is effected less by movement of the sleeve than the second camera output is effected by movement of the or said other sleeve. In other words, the rotational speed of a sleeve above which the first camera sensor portion can no longer produce substantially clear images of the surface thereof is faster than the rotational speed above which the second camera sensor portion can no longer produce substantially clear images of the surface thereof.

The field of view of the first camera sensor portion may be smaller than the field of view of the second camera sensor portion. The first camera sensor portion may comprise a first quantity of pixels and the second camera sensor portion may comprise a second, larger, quantity of pixels.

This provides that the scene viewable by the first camera sensor portion is smaller than the scene viewable by the second camera sensor portion. Advantageously, this provides that data indicative of the scene viewable by the first camera sensor portion is able to be processed faster than data indicative of the scene viewable by the second camera sensor portion.

The first and second camera sensor portions may respectively comprise different regions of a common optical sensing device. The first camera sensor portion may comprise a first quantity of pixels of an optical sensing device and the second camera sensor portion may comprise a second quantity of pixels of the same optical sensing device.

The first camera sensor portion may comprise a first quantity of pixels of a camera and the second camera sensor portion may comprise a second quantity of pixels of the same camera.

The first camera sensor portion may comprise a first camera and the second camera sensor portion may comprise a second camera.

The field of view of the first camera sensor portion and the field of view of the second camera sensor portion may not overlap.

The feature may correspond with an injection dose and may be marked on the or said other sleeve in the form of one of a plurality of markers, each marker being indicative of an amount of dose dialled or a dialled dose amount that remains to be delivered. At least some of the markers may comprise a numerical representation of an amount of dose dialled or a dialled dose amount that remains to be delivered.

This advantageously provides that the processor is able to determine an amount of dose dialled or a dialled dose amount that remains to be delivered.

The supplemental device may be configured such that, in use, a first plurality of features are caused to successively at least partially move through the field of view of the first camera sensor portion, and a second plurality of features are caused to successively at least partially move through the field of view of the second camera sensor portion, when the sleeve is rotated. In use, different parts of an injection device may be in alignment with the respective fields of view of the first and second camera sensor portions. For instance in use, a first plurality of features provided on a first sleeve may be caused to successively at least partially move through the field of view of the first camera sensor portion, and a second plurality of features provided on a second sleeve may be caused to successively at least partially move through the field of view of the second camera sensor portion.

The supplemental device may comprise a coupling arrangement for coupling the supplemental device to an injection device.

According to another aspect of the present invention there is provided a method of gathering information concerning the use of an injection device by a supplemental device, the method comprising:

a first camera sensor portion generating a first camera output indicative of a scene in the field of view of the first camera sensor portion;

a second camera sensor portion generating a second camera output indicative of a scene in the field of view of the second camera sensor portion; and at least one processor:

using the first camera output to determine whether a rotational speed of a sleeve of an injection device in the field of view exceeds a threshold speed;

if it is determined the rotational speed of the sleeve does not exceed the threshold speed, processing the second camera output to identify a feature marked on the or another sleeve; and if it is determined the rotational speed of the sleeve does exceed the threshold speed, refraining from attempting to determine the feature.

According to a further aspect of the present invention there is provided a computer program comprising machine readable instructions that when executed by a supplemental device comprising first and second camera portions and at least one processor control it to perform the foregoing method.

BRIEF DESCRIPTION OF THE FIGURES

The figures show:

FIG. 6 is a diagrammatic representation of how tick marks might appear in the field of view of the first camera at the beginning of a first camera exposure time;

FIG. 7 is a diagrammatic representation of how tick marks might appear in the field of view of the first camera at the end of the first camera exposure time; and FIG. 8 is a diagrammatic representation of information that may be analysed by a camera in another embodiment of the supplemental device.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
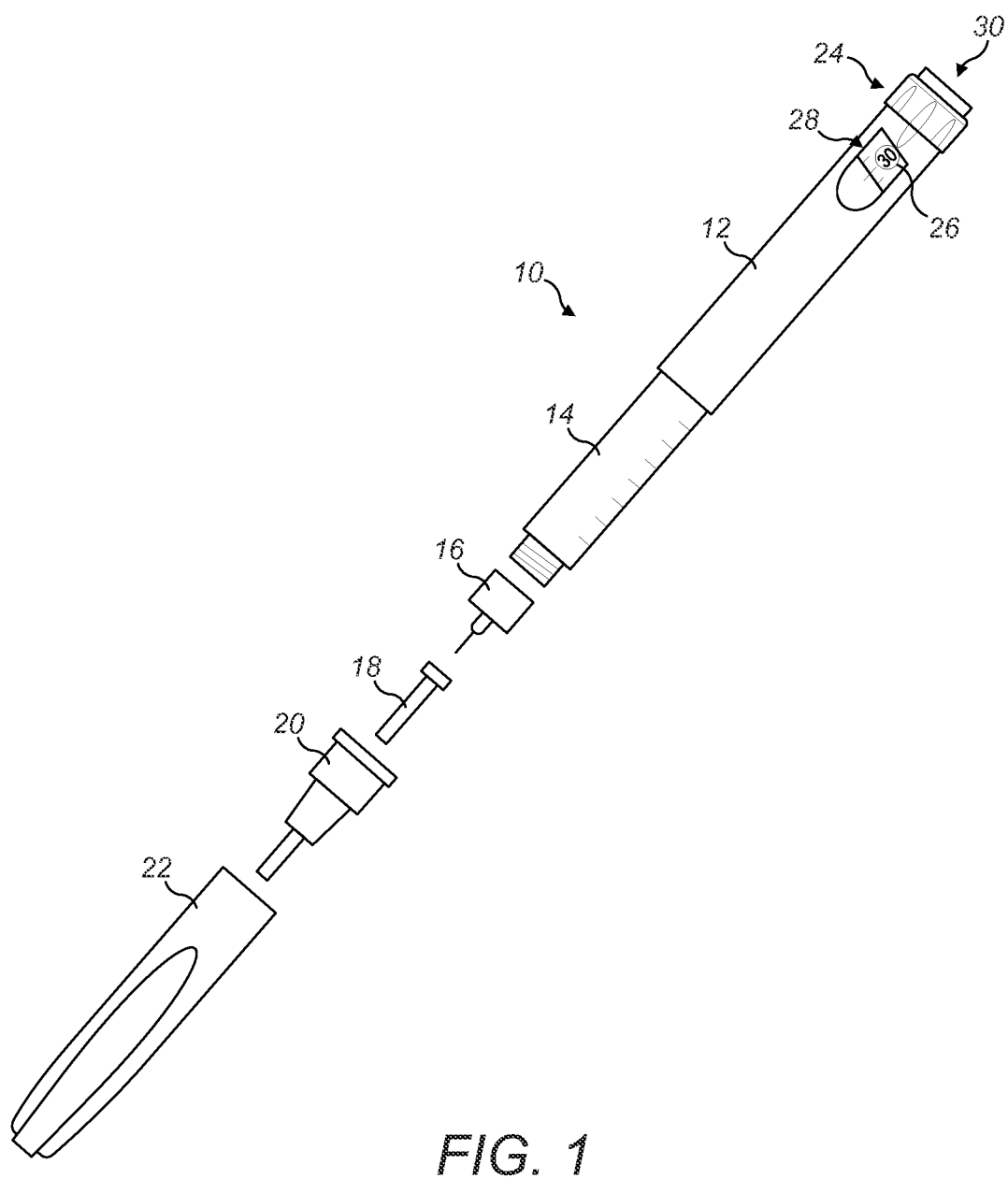
FIG. 1 is a schematic perspective view of an exemplary injection device.

FIG. 1 is an exploded view of an injection device 10, which may for instance represent the Solostar™ injection pen sold by Sanofi.

The injection device 10 of FIG. 1 is a pre-filled, disposable injection pen that comprises a housing 12 and contains an insulin container 14, to which a needle 16 can be affixed. The needle 16 is protected by an inner needle cap 18 and an outer needle cap 20, which in turn can be covered by a cap 22. An insulin dose to be ejected from injection device 10 can be selected by turning the dosage knob 24 (this act may be referred to as dialling an insulin dose). A feature such as a marker comprising a number 26 indicative of the selected dose (the dialled dose) is displayed via dosage window 28 in multiples of International Units (IU) for instance. An example of a dialled dose displayed in the dosage window 28 may be 30 IUs, as shown in FIG. 1.

The numbers 26 displayed in the dosage window 28 are printed on a sleeve (known as the number sleeve 17) contained in the housing 12 and which mechanically interacts with a piston inside the insulin container 14. When needle 16 is inserted into the skin of a patient and the injection button 30 is pushed, an amount of insulin corresponding to the dialled quantity displayed in the display window 28 is ejected from the injection device 10. During the course of the injection, as insulin leaves the injection device 10, the number sleeve 17 rotates. This causes the number 26 displayed in the dosage window 28 to change in accordance with the dialled amount of insulin yet to be dispensed. In other words, during the course of an injection the numbers 26 that successively align with the dosage window 28 are caused to count down.

Figure 2:
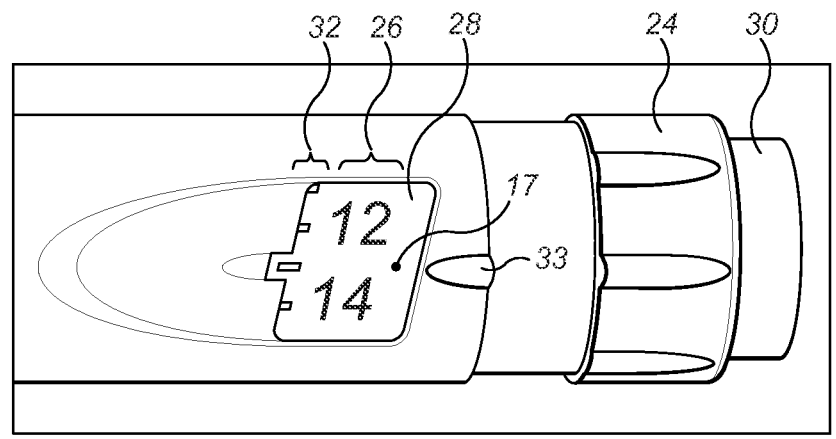
FIG. 2 is an enlarged view of an end of the injection device in FIG. 1.

FIG. 2 shows the dosage window 28 after 17 IUs of insulin have been delivered from the injection device 10 during the course of the injection in the preceding paragraph. It will be seen that a plurality of other features are provided on the number sleeve 17 adjacent the numbers 26. In this embodiment these features are markers comprising so-called tick marks 32. The tick marks 32 are substantially rectangular each having a width and a length that, in the embodiment in FIG. 2, extends along a direction parallel to the major axis of the injection device 10. Neighbouring tick marks 32 may be evenly spaced relative to one another although this is not necessary. By determining which tick mark 32 is in alignment with the indicator 33 a user is able to determine how much insulin has been dialled and, in the case of an injection, the dialled amount of insulin yet to be delivered.

In the example shown, an integer amount of insulin (measured in IUs) is associated with each respective tick mark 32 and the numbers 26 printed on the number sleeve 17 correspond with even amounts of insulin. Alternatively, however, other combinations of tick marks 32 and numbers 26 may be printed on the number sleeve 17. For instance a number 26 may be printed on the number sleeve 17 for every integer amount of insulin and only even amounts of insulin may be associated with a tick mark 32.

Regardless of the particular combination of tick marks 32 and numbers 26 used, persons familiar in the relevant art will appreciate that, when the number sleeve 17 is caused to rotate during dose dialling or during an injection, the respective tick marks 32 and numbers 26 move into and then out of view through the dosage window 28. Put another way, the tick marks 32 and numbers 26 move into and out of alignment with the dosage window 28.

Figure 3:
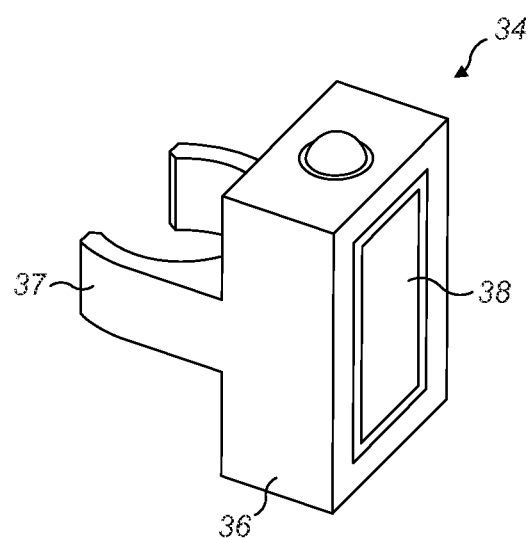
FIG. 3 is a schematic perspective view of a supplemental device according to one embodiment of the present invention.

FIG. 3 is a schematic illustration of a supplemental device 34 which may be releasably attached to an injection device such as the one depicted in FIG. 1. The supplemental device 34 comprises a housing 36 which is provided with a mating unit, coupling unit or connector 37 for embracing the housing 12 of an injection device 10. In particular the connector 37 may be configured to snap-fit onto the housing 12 of an injection device 10 in such a way that the device 34 can be subsequently removed therefrom. The connector 37 need not however be of the snap-fit variety and other arrangements may alternatively be suitable for coupling the supplemental device 34 to an injection device 10.

Figure 4:
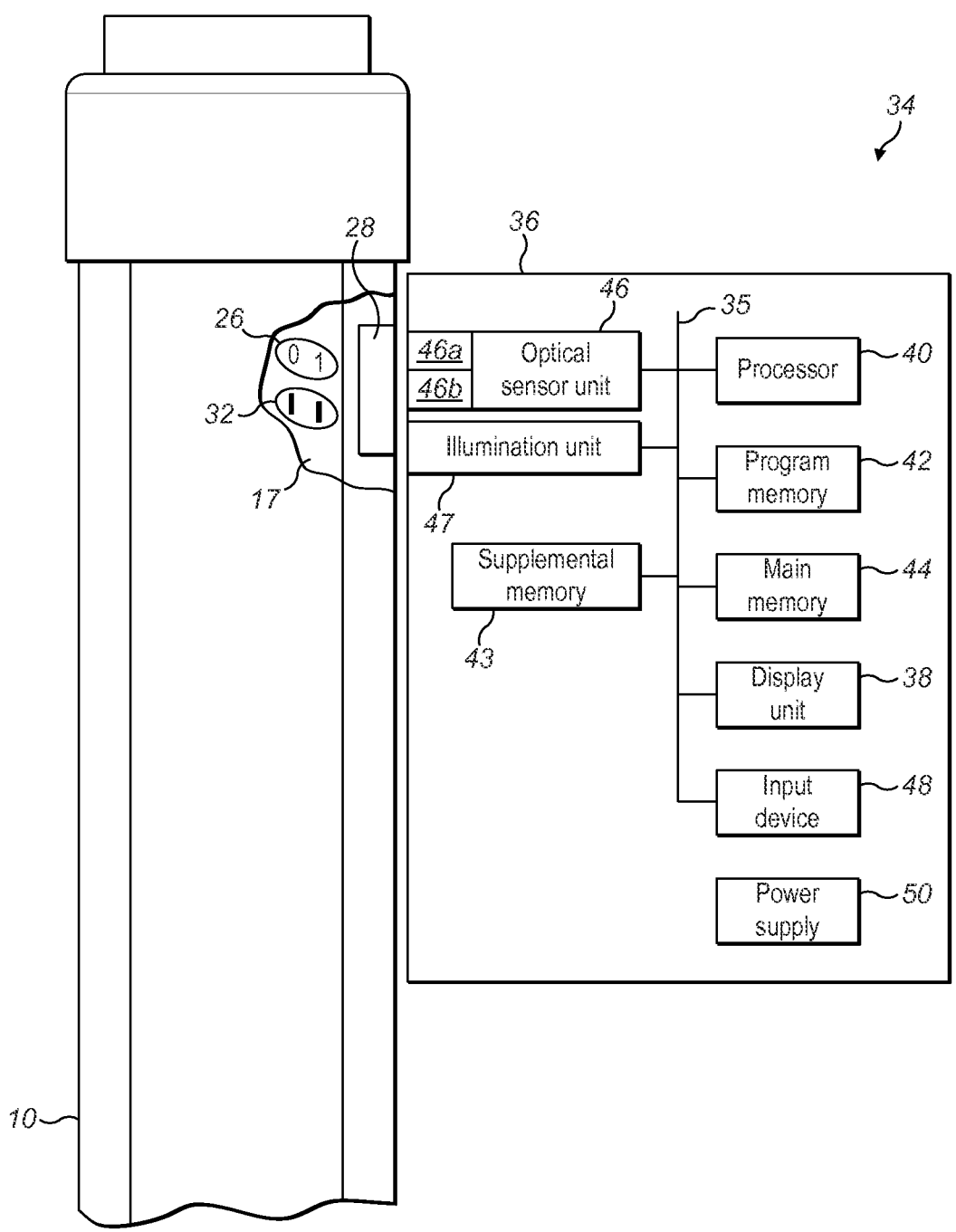
FIG. 4 is a schematic internal view of the supplemental device in FIG. 3.

When coupled to an injection device 10, the supplemental device 34 obstructs the dosage window 28 (as in FIG. 4). The supplemental device 34 contains at least one optical sensor for gathering information from the injection device 10. In particular the optical sensor(s) is(are) caused to gather information indicative of what is displayed in the dosage window 28. This gathered information is then capable of being processed for generating a dose history database. Such a dose history database may include records containing information about the various times at which insulin doses are administered and the quantity of insulin administered during each dose. The gathered information may also be processed for the purpose of displaying numbers 26 aligned with the dosage window 28 in larger format, for example by displaying numbers on a display unit which are larger than those provided on the number sleeve 17. This improves the readability of the amount of dose dialled or, in the case of an injection, the dialled dose amount yet to be delivered.

FIG. 4 illustrates an internal schematic view of the supplemental device 34 in a state where it is coupled to an injection device 10.

Within the housing 36 of the supplemental device 34, a variety of components are located and coupled together by a system bus 35. One such component includes a processor 40. Program memory 42 and main memory 44 are also coupled to the system bus 35. The processor 40 executes program code (e.g. software or firmware) stored in the program memory 42 and uses the main memory 44 to store intermediate results. The supplemental device 34 also comprises a supplemental memory 43 for storing the aforementioned dose history database. Program memory 42 may for instance be non-volatile memory such as Read-Only Memory. Main memory 44 may for instance be a volatile memory such as Random Access Memory, DRAM or SDRAM and supplemental memory 43 may for instance be Flash memory or an EEPROM or may comprise a memory card coupled to the system bus 35 via an interface such as a USB-type connection.

An optical sensor unit 46, also coupled to the system bus 35, is used to generate signals containing information indicative of what is displayed in the dosage window 28. The processor 40 may use these signals to determine delivered doses and generate the dose history database. The processor 40 may achieve this by executing an optical character recognition application to determine, from signals sent by the optical sensor unit 46, which number(s) 26 is(are) aligned with the dosage window 28. On the basis of such information the processor 40 then determines how much insulin has been dialled or, in the case of an injection, the dialled amount of insulin that remains to be delivered (or has already been delivered during the course of the injection).

Other components which may be coupled to the system bus 35 include an illumination unit 47, a display unit 38 and an input device 48. Such an illumination unit 47 may include one or more LEDs and may be controlled by the processor 40 to illuminate information displayed in the dosage window 28. An input device 48 (for example, a keypad) may be utilised by a user to interact with the supplemental device 34. Such an input device 48 may for instance be used to select one or more options displayed on a display unit 38. In some embodiments a display unit 38 may be provided with touch-screen functionality thus enabling it to function as both an output device and the input device 48.

A power supply source 50 (for example a battery) is for powering the various components of the supplemental device 34.

Details of the optical sensor unit 46 will now be outlined in further detail.

Figure 5:
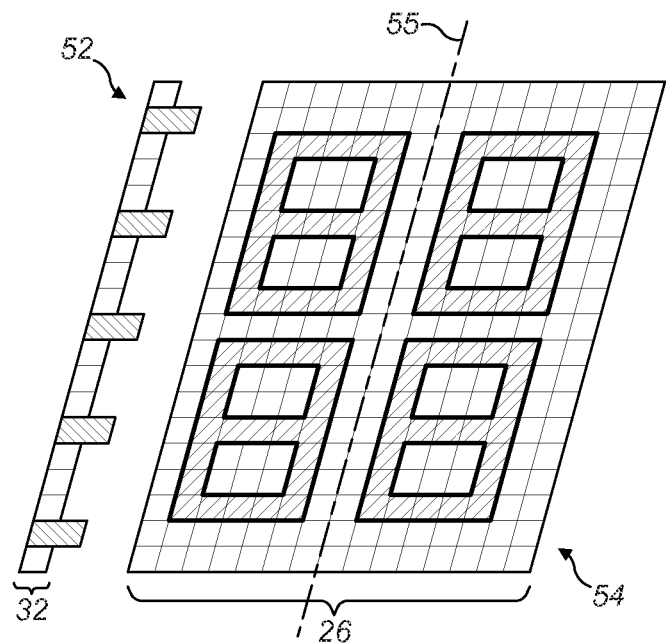
FIG. 5 is a diagrammatic representation of the information analysed by the respective cameras of the supplemental device in FIGS. 3 and 4.
Figure 5A:
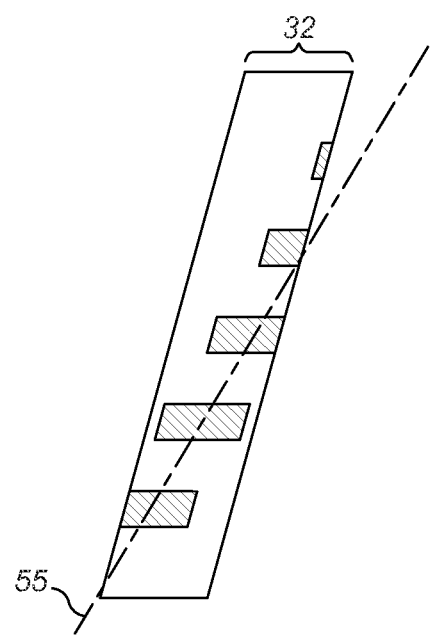
FIG. 5a is a diagrammatic representation of information that may be analysed by a camera of the supplemental device in FIGS. 3 and 4.

The optical sensor unit 46 comprises first and second cameras 46a, 46b. The first camera 46a comprises a first plurality of pixels 52 and has a first field of view of the dosage window 28 in use. The second camera 46b comprises a second plurality of pixels 54 and has a second field of view of the dosage window 28 in use. Looking at FIG. 5, the first plurality of pixels 52 is fewer in number than the second plurality of pixels 54. This provides that, the first camera 46a may comprise a linear sensor and that the second camera 46b may comprise a matrix sensor. The linear sensor is orientated substantially parallel to an axis along which markers on the number sleeve 17 are caused to move when a dose is dialled or dispensed. In the example of FIG. 5 numbers 26 on the number sleeve 17 are caused to move along axis 55 when a dose is dialled or dispensed. The linear sensor may thus extend parallel to this axis of movement or be partially diagonal relative thereto as shown in FIG. 5a.

In use the supplemental device 34 utilises the first camera 46a to generate first camera output indicative of what is displayed in its field of view. Such camera output is generated at a first rate which may, for instance, be at least ten times per second (regardless of whether the rate is periodic or irregular). In the embodiment shown in FIG. 5, the supplemental device 34 is configured such that, when in use, tick marks 32 are caused to successively move through the field of view of the first camera 46a when the number sleeve 17 of an injection device rotates during dose dialling or dose delivery. As a result, the first camera output is indicative of the particular tick marks 32 aligned with the dosage window 28 in the field of view of the first camera 46a.

In use the supplemental device 34 is capable of utilising the second camera 46b to generate second camera output indicative of what is present in its field of view. Such camera output is generated at a second rate which may, for instance, be at least three times per second (regardless of whether the rate is periodic or irregular). In the embodiment shown in FIG. 5, the supplemental device 34 is configured such that, when in use, numbers 26 are caused to successively move through the field of view of the second camera 46b when the number sleeve 17 of an injection device 10 rotates during dose dialling or dose delivery. As a result, the second camera output is indicative of the particular number(s) 26 aligned with the dosage window 28 in the field of view of the second camera 46b.

Upon comparing FIGS. 2 and 5 the respective areas of the dosage window 28 encompassed by the fields of view of the first and second cameras 46a, 46b in the present example will be apparent. How the first and second camera outputs are subsequently used will now be explained.

With regards to the first camera output, the processor 40 utilises this information to monitor the rotational speed of the number sleeve 17. Although there are various ways of doing so, this might be enabled by the processor 40 performing an analysis of the contrast of images produced by the first camera 46a. If a measure of contrast is determined to be less than a predetermined value, then the sleeve 17 is considered to be rotating above a threshold speed. This is described in more detail as follows.

In the embodiment shown in FIG. 2, the sleeve is white and the tick marks 32 are black. The time it takes for the first camera 46a to gather information for the purpose of generating first camera output is referred to hereafter as the first camera exposure time $t_{exposure}$. If the injection device 10 is not in use then, during a first camera exposure time $t_{exposure}$, the sleeve 17 will not have rotated. Upon analysing first camera output indicative of how the sleeve 17 appears in the field of view during this exposure time $t_{exposure}$, processor 40 will determine that some areas of the sleeve 17 appeared black (i.e. where the tick marks 32 are located) and that some areas of the sleeve appeared white (i.e. where the tick marks 32 are not located). The contrast between such black and white areas has a high value, and is the maximum contrast detectable by the processor 40 for a given illumination. Thus for a particular first camera exposure time $t_{exposure}$ if the processor 40 determines that a measure of contrast of the image from the first camera 46a is high, the processor will determine that during such exposure time the sleeve 17 was not rotating.

If the injection device 10 is in use, for example a dose is being dialled or $t_{exposure}$ dispensed, then during a particular first camera exposure time $t_{exposure}$ the sleeve 17 will have rotated. During such a first camera exposure time $t_{exposure}$ when the injection device 10 is in use, part of a tick mark 32, and part of the sleeve 17 where no tick mark 32 is located, will move through an area in the field of view. In other words, both black and white areas on the sleeve 17 will move through an area in the field of view. Pixels used to generate camera output indicative of what appears in this part of the field of view will output camera output signals indicative that during the first camera exposure time $t_{exposure}$ the sleeve 17 appeared grey.

With the foregoing in mind it will be appreciated that the sleeve 17 may be caused to rotate at a speed such that during a first camera exposure time $t_{exposure}$ only some pixels are exposed to both black and white areas. The other pixels during the course of that exposure time $t_{exposure}$ are exposed to areas on the sleeve 17 comprising the same colour. FIGS. 6 and 7 illustrate how tick marks 32 may be caused to move through the field of view of the first camera 46 during a first camera exposure time $t_{exposure}$.

FIG. 6 illustrates how tick marks 32 appear in the field of view at the $t_{exposure}$ beginning of the first camera exposure time $t_{exposure}$ and FIG. 7 illustrates how such tick marks 32 appear in the field of view at the end of the first camera exposure time $t_{exposure}$. The tick marks move downwards in the direction shown in the Figures, and the mark shown uppermost in FIG. 6 is the mark shown lowermost in FIG. 7. In this example, during the first camera exposure time $t_{exposure}$ the pixels denoted as A, C, D, E, G, H, I and K are exposed to both black and white areas on the sleeve 17. The pixels denoted B, F and J are exposed to the same colour (white in the case of B and J and black in the case of F). Thus upon analysing first camera output associated with this exposure time $t_{exposure}$ the processor 40 determines that the sleeve 17 appeared grey on average to pixels A, C, D, E, G, H, I and K, although different shades of grey because of the different proportion of the exposure time for which the tick mark was incident with the relevant pixel during the first camera exposure time. However, from the outputs associated with pixels B, F and J the processor 40 determines that during the exposure time $t_{exposure}$ there is a high contrast only between non-adjacent pixels B and F and between non-adjacent pixels F and J, and a lower contrast is present between other pixel pairs.

When the sleeve 17 is caused to rotate even more quickly, each pixel 52 of the first camera 46a (denoted A to K in the example of FIGS. 6 and 7) is exposed to both black and white areas of the sleeve 17 during a first camera exposure time $t_{exposure}$. Thus upon analysing first camera output associated with such an exposure time $t_{exposure}$ the processor 40 will determine that the sleeve 17 appeared grey on average to all pixels 52 during the first camera exposure time $t_{exposure}$. As such, the processor 40 determines that the measure of contrast in the image is low, and is significantly lower than the maximum detectable contrast (i.e. the difference between black and white).

A measure of speed of rotation of the number sleeve 17 may be obtained by the processor 40 in any suitable way. It may for instance involve detecting the sharpness of edges, by analysing the transition between black and white portions in the first camera output image. It may alternatively involve an analysis of the total number of pixels, for instance determining a number or proportion of pixels that are neither black nor white but grey. Grey pixels can be identified for instance as having a luminance value that is between two thresholds defined by maximum (white) and minimum (black) luminance values. The thresholds may for instance cause pixels having luminance values between 20% and 80% of the maximum and minimum to be gray pixels. Alternatively, the maximum and minimum values may be predefined and not based on a particular first camera output.

When the processor 40 determines that the number sleeve 17 is not rotating above the threshold speed the processor 40 utilises second camera output received from the second camera 46b. Such output is indicative of which number(s) is (are) aligned with the dosage window 28 of the injection device 10 in the field of view of the second camera 46b. As previously mentioned, the processor 40 utilises this output to determine the dose displayed in the dosage window 28. This relates to the amount of insulin dialled or, during the course of an injection, the amount of insulin yet to be dispensed. In the embodiment shown in FIG. 5 this is achieved by the processor 40 implementing optical character recognition functionality to determine which particular number(s) 26 is(are) in the field of view of the second camera 46b. On the basis of such information the processor 40 then determines the dialled amount of insulin or, during the course of an injection, the dialled amount of insulin that remains to be delivered (or has already been delivered during the course of the injection).

Moreover, the processor 40 utilises the first camera output to continually monitor the rotational speed of the number sleeve 17. When a determination is made that the number sleeve 17 is rotating in excess of the threshold speed the processor 40 refrains from attempting to analyse the second camera output for determining a dose marked on the sleeve 17. However once the processor 40 determines that the number sleeve 17 is rotating below the threshold speed, by utilising the first camera output, the processor 40 once again starts utilising the second camera output. In other words the processor 40 once again starts using the second camera output to determine the amount of insulin dialled or, during the course of an injection, the amount of insulin yet to be dispensed (or how much insulin has already been dispensed during the injection).

By refraining from processing the second camera sensor output when the number sleeve 17 is moving too quickly, the power consumption of the supplemental device 2 can be reduced. Moreover, if the threshold speed is selected appropriately, this is achieved without any reduction in performance since the processor 40 would not reliably be able to identify the numerals in the field of view of the second camera sensor.

The heretofore described operation of the first and second cameras 46a, 46b, and the processing of their respective camera outputs, is realised by the processor 40 operating in accordance with instructions contained in an operation application stored in the program memory 42.

The first camera 46a is able to generate camera output at faster rate than the second camera 46b because the first camera 46a is more sensitive to light. More specifically the first camera 46a comprises a fast sensor and the second camera 46b comprises a slow sensor. Thus, for a given amount of illumination it takes less time for the first camera 46a (the fast sensor) to generate camera output, from which a reliable image of the number sleeve 17 may be generated, than the second camera 46b (the slow sensor). One way to increase the threshold speed above which numbers 26 appear blurry to the second camera 46b is to increase the level of illumination of the dosage window 28 using illumination unit 47 for example. This provides that for a given exposure time, more light is incident on the second camera 46b thereby allowing the second camera 46b to generate, in a shorter period of time, camera output from which a reliable image of the number sleeve 17 may be generated. However increasing illumination levels disadvantageously increases power consumption. The embodied arrangements provide that reliable measures of dose may be determined by the processor 40 without increasing illumination levels of the dosage window 28.

It should be noted that although the first and second cameras 46a, 46b may comprise separate devices, in alternative embodiments they may instead comprise different regions of a common optical sensing device. For instance the first and second cameras 46a, 46b may comprise respective cameras provided on the same substrate. Alternatively, the first camera 46a may comprise a first plurality of pixels of a CCD device and the second camera 46b may comprise a second plurality of pixels of the same CCD device. More specifically, the first camera 46a may comprise a first camera sensor portion of a camera, and the second camera 46b may comprise a second camera sensor portion of the same camera.

In the example described in this specification with reference to FIGS. 2 and 5 the features provided on the number sleeve 17 are markers and comprise numbers 26 and tick marks 32. However the present invention is not limited to use with such a number sleeve 17. For example, instead of numbers 26 the features on the number sleeve 17 may be markers that comprise a plurality of letters, symbols or respective sections of a code. Such markers may be printed on, be engraved into, or protrude from the number sleeve 17. The processor 40 may be configured to determine from second camera output corresponding to such letters, symbols or code sections an amount of dose dialled or, during the course of an injection, the dialled amount of dose yet to be delivered (or has already been delivered during the course of the injection). Also instead of tick marks 32 of the kind mentioned herein being provided on a number sleeve 17, the number sleeve 17 may be provided with other features such as other markers that are provided for a similar purpose for example a series of dots, corrugations and/or protrusions on the number sleeve 17, a bar code or any combination thereof.

In embodiments in which the number sleeve 17 is provided with one or more symbols indicative of the amount of dose dialled or delivered, instead of implementing OCR functionality the supplemental device 34 may instead implement pattern recognition functionality to determine from such symbols the corresponding amount of dose dialled or delivered.

Furthermore, notwithstanding the foregoing, a supplemental device 34 may be configured to function with an injection device 10 having a number sleeve 17 with only one set of markers. The number sleeve 17 of such an injection device may not be provided with both tick marks 32 and, separately, numbers 26 (or any other such markers e.g. letters, symbols or code) for example. Instead the number sleeve 17 of such an injection device may be provided with a single set of symbols. Part of each such symbol may be present in the field of view of the first camera 46a when the number sleeve 17 rotates and at the same time another part of each such symbol may be present in the field of view of the second camera 46b. Pattern recognition functionality may be used in the manner aforementioned to determine from what is present in the field of view of the second camera 46b the amounts of dose dialled or delivered. What is present in the field of view of the first camera 46a may be used for the same purpose as the tick marks 32 heretofore described. More specifically, the part of each symbol which passes through the field of view of the first camera 46a as the number sleeve 17 rotates may be used to monitor the rotational speed of the sleeve.

It will be appreciated that the number sleeve 17 of an injection device 10 does not need to be white and the markers (for example numbers 26) do not need to be black. They may instead be any colour provided that the supplemental device 34 is able to distinguish between such colours.

Although in the above the rates at which outputs from the first camera sensor and the second camera sensor are reviewed are different, they may instead be the same.

Also, although in the above the second camera sensor is continually activated and the second camera output is not processed if the rotation speed of the number sleeve 17 is above the threshold, instead the second camera sensor may be controlled not to provide a second camera output when this condition is present. This can further reduce power consumption.

Furthermore, the optical sensor unit 46 (see FIG. 4) may comprise a single camera that includes a plurality of pixels 53. In use, markers on the number sleeve 17 (e.g. numbers, symbols etc.) are caused to move through the field of view of the pixels 53. The camera generates camera output indicative of a scene in the field of view of the pixels 53. In one operational mode the processor 40 analyses camera output relating to a subset of the pixels 53a only. In another operational mode the processor 40 analyses camera output relating to all of the pixels 53.

The subset of pixels 53 may comprise a row of pixels 53a that is substantially parallel to the axis along which markers on the number sleeve 17 are caused to move when a dose is dialled or dispensed. In the example of FIG. 8, numbers 26 are caused to move along axis 55 when a dose is dialled or dispensed.

In one operational mode the processor 40 uses camera output relating to the subset of pixels 53a only. Such camera output is used to determine whether the number sleeve 17 is rotating above a threshold speed. The processor 40 may make such a determination by performing an analysis of the contrast of images produced using camera output relating only to the subset of pixels 53a. This analysis may be in accordance with the manner previously described.

If the number sleeve 17 is determined to be rotating above a threshold speed then the processor 40 continues to monitor the rotational speed using output from the subset of pixels 53a only. If the rotational speed is subsequently determined to be no longer in excess of the threshold speed then another operational mode is entered. In this operational mode the processor 40 uses the total camera output, or in other words the camera output relating to each of the pixels 53.

In this mode the total camera output is used to continue monitoring the rotational speed of the number sleeve 17 as well as to determine an amount of dose dialled or, in the case of an injection, an amount of dose yet to be dispensed (or an amount that has already been dispensed during the course of the injection). This is achieved by the processor 40 performing two separate analyses. One such analysis involves the processor 40 determining what particular markers (e.g. numbers) are present in the field of view of the total amount of pixels 53. This may be achieved by implementing pattern or character recognition functionality as already discussed. The other such analysis involves using camera output relating only to the subset of pixels 53a to continue monitoring whether the rotational speed of the number sleeve 17 exceeds the threshold amount.

If the rotational speed of the number sleeve 17 is not determined to exceed the threshold amount then the processor 40 continues to perform the two separate analyses. However if the rotational speed of the number sleeve 17 is determined to be in excess of the threshold then the processor 40 refrains from performing the two separate analyses and reverts back to only using camera output that relates to the subset of pixels 53a in order to monitor the rotational speed of the number sleeve. In other words the processor refrains from utilising the total camera output and reverts back to using only the camera output which relates to the subset of pixels 53a.

Throughout this specification, examples of the supplemental device 34 in use have been given with reference to a Solostar™ injection pen of the kind in FIG. 1. With reference to FIG. 2 it will be appreciated that the dosage knob 24 moves relative to the dosage window 28 when a dose is dialled or dispensed. However, as already stated, a supplemental device 34 of the present invention is not restricted to use with a Solostar™ injection pen and may be used with other types of injection devices. One such injection device may be similar to the Solostar™ injection pen but the dosage knob thereof may not translate relative to the dosage window. In such an injection device the dosage knob comprises an external sleeve that moves rotationally only in accordance with an amount of dose dialled and/or dispensed. In other words when a dose is dialled or dispensed the dosage knob rotates at a speed corresponding to that at which medicament is being dialled or delivered from the injection device respectively. A supplemental device 34 may utilise features provided on the dosage knob of such an injection device for the same purpose as the tick marks 32 in FIG. 2. These features may for instance comprise corrugations for enhancing a user's grip of the dosage knob. It will be appreciated that features on the dosage knob are caused to move through the field of view of the first camera 46a when a dose is dialled and/or dispensed. Furthermore, features provided on the number sleeve 17 such as numbers of the kind in FIG. 2 are caused to move through the field of view of the second camera 46b when a dose is dialled and/or dispensed. The output of the first and second cameras 46a, 46b is used in a similar manner to that heretofore described to monitor the rotational speed of a number sleeve of the injection device and to determine an amount of dose dialled or, in the case of an injection, the amount of dose that has been delivered (or is yet to be delivered during the course of the injection).

With reference to FIGS. 5 and 8, it will be appreciated that in some embodiments the area of the number sleeve 17 analysed may not include two sets of numbers. In other words in the examples of FIGS. 5 and 8 the sensors have a field of view that is wide enough for two numbers (e.g. "88" and "88") to occupy the field of view at a given time. However the teachings of the present invention equally apply in the case that the field of view is such that only a single number (e.g. "88") may be present in the field of view.

Lastly, it will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A supplemental device for gathering information concerning the use of an injection device, the supplemental device comprising:
   a first camera sensor portion for generating a first camera output indicative of a scene in the field of view of the first camera sensor portion;
   a second camera sensor portion for generating a second camera output indicative of a scene in the field of view of the second camera sensor portion; and
   at least one processor configured:
   to use the first camera output to determine whether a rotational speed of an object in the field of view exceeds a threshold speed;

if the rotational speed of the object does not exceed the threshold speed, to process the second camera output to identify a feature provided on the or another object; and if the rotational speed of the object does exceed the threshold speed, to refrain from attempting to identify the feature.

2. The supplemental device of claim 1, wherein the first camera sensor portion generates first camera output at a first rate and the second camera sensor portion generates second camera output at a second, slower, rate.

3. The supplemental device of claim 1, wherein the field of view of the first camera sensor portion is smaller than the field of view of the second camera sensor portion.

4. The supplemental device of claim 1, wherein the first camera sensor portion comprises a first quantity of pixels and the second camera sensor portion comprises a second, larger, quantity of pixels.

5. The supplemental device of claim 1, wherein the first and second camera sensor portions respectively comprise different regions of a common optical sensing device.

6. The supplemental device of claim 5, wherein the first camera sensor portion comprises a first quantity of pixels of an optical sensing device and the second camera sensor portion comprises a second quantity of pixels of the same optical sensing device.

7. The supplemental device of claim 6, wherein the first camera sensor portion comprises a first quantity of pixels of a camera and the second camera sensor portion comprises a second quantity of pixels of the same camera.

8. The supplemental device of claim 1, wherein the first camera sensor portion comprises a first camera and the second camera sensor portion comprises a second camera.

9. The supplemental device of claim 1, wherein the field of view of the first camera sensor portion and the field of view of the second camera sensor portion do not overlap.

10. The supplemental device of claim 1, wherein the feature corresponds with an injection dose and is marked on the or said other object in the form of one of a plurality of markers, each marker being indicative of an amount of dose dialled or a dialled dose amount that remains to be delivered.

11. The supplemental device of claim 10, wherein at least some of the markers comprise a numerical representation of an amount of dose dialled or a dialled dose amount that remains to be delivered.

12. The supplemental device of claim 1, wherein the supplemental device is configured such that, in use, a first plurality of features are caused to successively at least partially move through the field of view of the first camera sensor portion, and a second plurality of features are caused to successively at least partially move through the field of view of the second camera sensor portion, when the object is rotated.

13. The supplemental device of claim 1, wherein the or said other object comprises a sleeve of an injection device.

14. The supplemental device of claim 1, further comprising a coupling arrangement for coupling the supplemental device to an injection device.

15. A method of gathering information concerning the use of an injection device by a supplemental device, the method comprising:

a first camera sensor portion generating a first camera output indicative of a scene in the field of view of the first camera sensor portion;

a second camera sensor portion generating a second camera output indicative of a scene in the field of view of the second camera sensor portion; and at least one processor:

using the first camera output to determine whether a rotational speed of an object in the field of view exceeds a threshold speed;

if the rotational speed of the object does not exceed the threshold speed, processing the second camera output to identify a feature provided on the or another object; and if the rotational speed of the object does exceed the threshold speed, refraining from attempting to identify the feature.

16. A non-transitory computer-readable medium comprising machine readable instructions that when executed by a supplemental device comprising first and second camera sensor portions and at least one processor control it to perform the method of claim 15.

* * * * *